United States Patent [19]

Blank et al.

[11] Patent Number: 4,769,454

[45] Date of Patent: Sep. 6, 1988

[54] PROCESS FOR THE PREPARATION OF N-METHYLOL-CAPROLACTAM

[75] Inventors: Heinz-Ulrich Blank, Odenthal-Gloebusch; Wolfgang Bauer, Leverkusen, both of Fed. Rep. of Germany

[73] Assignee: Bayer Aktiengesellschaft, Leverkusen, Fed. Rep. of Germany

[21] Appl. No.: 141,183

[22] Filed: Jan. 6, 1988

[30] Foreign Application Priority Data

Jan. 9, 1987 [DE] Fed. Rep. of Germany ....... 3700451

[51] Int. Cl.⁴ .......................................... C07D 223/10
[52] U.S. Cl. ..................................................... 540/531
[58] Field of Search ........................................ 540/531

[56] References Cited

U.S. PATENT DOCUMENTS 4,185,017  1/1980  Piesch et al. ...................... 540/531
4,620,949  11/1986  Lin ..................................... 540/531

FOREIGN PATENT DOCUMENTS 666431  7/1963  Canada ............................... 540/531
285927  5/1969  U.S.S.R. ............................. 540/531

*Primary Examiner*—Robert T. Bond
*Attorney, Agent, or Firm*—Sprung Horn Kramer & Woods

[57] ABSTRACT

The process for the preparation of N-methylolcaprolactam through reaction of caprolactam with formaldehyde in the presence of an alkaline catalyst at elevated temperature is essentially improved when the reaction is carried out substantially solvent-free at 70° to 100° C. In an advantageous fashion, the alkaline catalyst used is in heterogeneous form. In a furthermore advantageous fashion, seed crystals of pure N-methylolcaprolactam are added to the reaction batch after cooling to a temperature below the melting point of pure N-methylolcaprolactam.

20 Claims, No Drawings

PROCESS FOR THE PREPARATION OF N-METHYLOL-CAPROLACTAM

BACKGROUND OF THE INVENTION

1. Field of the Invention

The present invention relates to an improved process for the preparation of N-methylol-caprolactam through reaction of caprolactam with formaldehyde in the presence of an alkaline catalyst at elevated temperature.

2. Description of the Related Art

It has already been disclosed that N-methylolcaprolactam can be prepared in a yield of 67% of the theoretical yield from caprolactam and excess paraformaldehyde (50% excess) in 95% strength ethanol in the presence of 4.2 mol % of sodium hydroxide as catalyst (J. Am. Chem. Soc. 70 (1948), 2115–2118). The reaction specified is carried out in approximately 50% strength solution.

The procedure mentioned for the preparation of N-methylol-caprolactam is also in Houben-Weyl, Methoden der organischen Chemie [Methods of Organic Chemistry], 4th edition, vol. XI/2/1958) p. 570, but it is stated here that it was not possible to reproduce the procedure cited, and a yield of only 50% of the theoretical yield was achieved. A very similar procedure is furthermore given in DE-OS (German Published Specification) No. 2,616,374, likewise in only 50% of the theoretical yield. A short note on the preparation of N-methylolcaprolactam as a simple intermediate in the preparation of further caprolactam derivatives is furthermore found in Arch. Pharm. 294 (1961), pp. 344–348. However, only the starting materials caprolactam and paraformaldehyde are mentioned in this note; further notes on the reaction parameters are omitted. The N-methylol-caprolactam is obtained as an oil in this procedure; there is no mention of characterization and the yield of the N-methylol-caprolactam prepared.

U.S. Pat. No. 3,073,843 furthermore gives a preparation procedure for a formally similar compound, namely N-methylol-pyrrolidone, in which procedure potassium hydroxide was added to pyrrolidone, whereupon a suspension of potassium pyrrolidone is formed in the remaining pyrrolidone. Paraformaldehyde is then added, which leads to a spontaneous increase in temperature to 80° C. The yield is given as essentially quantitative. However, this process cannot be applied to caprolactam since (a) in contrast to caprolactam, 2-pyrrolidone becomes liquid at an only slightly elevated temperature;

(b) the 5-membered ring system of 2-pyrrolidone and 7-membered ring system of caprolactam have different reactivities. Thus, the reaction mixture according to U.S. Pat. No. 3,073,843 warms spontaneously to about 80° C., whereas the mixture of caprolactam, paraformaldehyde and potassium hydroxide has to be melted initially by supplying energy and then brought to a suitable reaction temperature and kept there while supplying further energy;

(c) N-methylol-caprolactam is thermally labile, whereas, in contrast to this, N-methylol-pyrrolidone is a stable compound.

SUMMARY OF THE INVENTION

Surprisingly, it has now been found that N-methylol-caprolactam can be prepared in yields which are far above those of the literature when the reaction is carried out substantially solvent-free.

A process has been found for the preparation of N-methylol-caprolactam (N-hydroxymethyl-caprolactam) through reaction of caprolactam with formaldehyde in the presence of an alkaline catalyst at elevated temperature, which process is characterized in that the reaction is carried out substantially solvent-free at a temperature of 70° to 100° C.

DETAILED DESCRIPTION OF THE INVENTION

The process according to the invention is carried out substantially solvent-free. Substantially solvent-free here means the use of OH group-containing solvents, such as $H_2O$ or $C_1$–$C_4$-alkanols (methanol, ethanol, propanol, isopropanol, butanol or isobutanol; preferably methanol or ethanol) to a maximum of 10% by weight, for example 0.01 to 10% by weight, preferably 0.01 to 5% by weight, relative to the total reaction batch, the use of aprotic solvents, such as aliphatic or aromatic hydrocarbons or aliphatic or aromatic halogenohydrocarbons (hexane, heptane, octane, isooctane, dodecane, isododecane, benzene, toluene, xylene, chlorobenzene, dichlorobenzene, methylene chloride, chloroform, carbon tetrachloride, halogenated ethanes or propanes and the like), to a maximum of 20% by weight, for example 0.01 to 20% by weight, preferably 0.01 to 10% by weight, relative to the total reaction batch, or the complete omission of solvents or diluents. In the case where a solvent or diluent is to be employed, it is also possible to employ a mixture of the solvents mentioned. An aprotic solvent (mixture) is preferably employed or the process is carried out without solvents or diluents. The procedure without any solvents or diluents is particularly preferred.

Suitable alkaline catalysts are inorganic compounds which react in an alkaline manner, such as the hydroxides of alkali metals or of alkaline-earth metals, and the salts of weak inorganic acids of the alkali metals, and also organic compounds which react in an alkaline manner, such as tertiary aliphatic amines, for example triethylamine. In a preferred fashion, alkaline catalysts are used which can be incorporated in solid form into the reaction mixture and are present in heterogeneous form during the reaction. These are, for example, the mentioned hydroxides of alkali metals or of alkaline-earth metals and the salts of weak inorganic acids of alkali metals. Such salts of weak inorganic acids are, for example, sodium tetraborate (borax), sodium carbonate (soda) and potassium carbonate (potash). Of these, carbonates are preferably employed and potassium carbonate is particularly preferably employed.

The alkaline catalyst is employed in amounts from 0.1 to 2.5 mol %, preferably 0.25 to 1.5 mol %, particularly preferably 0.5 to 1.0 mol %, relative to caprolactam.

The process according to the invention is carried out at a temperature from 70° to 100° C., preferably 70° to 90° C., particularly preferably 70° to 80° C. In this form, the process according to the invention gives yields of 80% and more of the theoretical yield.

It has furthermore been found that the yield can be further increased to greater than 95% of the theoretical yield if seed crystals of pure N-methylol-caprolactam are added to the reaction batch after cooling to a temperature below the melting point of pure N-methylol-caprolactam. The melting point of N-methylol-caprolactam is taken here to be a temperature of 65° to 66° C. It is very surprising that the seeding described makes it possible not only to obtain the N-methylol-caprolactam more quickly in crystalline form, but also that a higher conversion and thus yield are achieved without it hitherto being possible to explain the mechanism of this process. The seeding described thus represents a preferred embodiment of the process according to the invention.

The seeding is carried out at a temperature below the melting point of pure N-methylol-caprolactam, preferably at 10° to 65° C., particularly preferably at 20° to 60° C. and very particularly preferably at 30° to 55° C. The seed crystals are added to the reaction batch, cooled in the manner mentioned, in an amount from 0.0001 to 10% by weight, preferably 0.001 to 5% by weight, particularly preferably 0.1 to 1% by weight, relative to the total reaction batch.

The process according to the invention can be carried out, for example, by premixing caprolactam, formaldehyde and the catalyst and introducing this mixture in portions into a preheated reaction vessel with melting. Any solvent or diluent which is co-used can be initially introduced or premixed with the substances mentioned, but alternatively can be added separately. The formaldehyde chosen is an anhydrous form, for example paraformaldehyde or trioxane, preferably paraformaldehyde. In order to achieve high yields, an approximately equimolar mixture of caprolactam and formaldehyde is employed. Of course, it is also possible to deviate from an equimolar ratio of caprolactam and formaldehyde, but this leads, in a known fashion, to incomplete conversion of the substance employed in excess. The molten mixture is then brought to the reaction temperature with stirring.

After cooling the reaction batch to a temperature below the melting point of pure N-methylol-caprolactam, seed crystals of pure N-methylol-caprolactam are added to the reaction batch in the manner described.

EXAMPLES 1 TO 7

All batches were carried out in four-necked flasks fitted with internal thermometers, stirrers and refulx condensers.

Caprolactam, paraformaldehyde and the catalyst were premixed and introduced in portions into the heated flask with melting. The reaction temperature was 75° C., and the reaction time was $\leq 2$ hours, with the exception of Example 7. The reaction mixture was transferred into bottles after the reaction and after cooling. The yield and conversion were determined using high-pressure liquid chromatography (HPLC) and by means of the NMR spectrum.

EXAMPLE 1

1,130 g (10.00 mol) of 6-caprolactam, 306.1 g (10.00 mol) of 98% purity paraformaldehyde and 6.91 g (0.05 mol) of ground $K_2CO_3$ were brought to reaction. Apart from the catalyst, a clear solution was present. After 2 hours, the mixture was cooled to 50° C.; a few grains of pure N-methylol-caprolactam were added as seed crystals. 1,428 g of methylolcaprolactam (=99.9% of the theoretical yield) were obtained.

EXAMPLE 2

113 g (1.00 mol) of 6-caprolactam, 30.6 g (1.00 mol) of 98% purity paraformaldehyde and 3.45 g (0.025 mol) of $K_2CO_3$ were brought to reaction. After reacting for 0.5 hours at 75° C., the solution, which was clear apart from the catalyst, was cooled to 50° C., and 0.5% (relative to the total batch) of seed crystals were then added. 147 g of crystallized reaction mixture (94.4% purity material)=139 g of methylolcaprolactam=96,9% of theoretical yield were obtained.

EXAMPLE 3

The procedure as in Example 1 was carried out, but the $K_2CO_3$ catalyst was added as a 33% strength aqueous solution and the reaction time was reduced to 0.5 hours. In a 1 molar batch, 123 g of methylolcaprolactam=86% of the theoretical yield were obtained as an oil.

EXAMPLE 4

113 g (1.00 mol) of 6-caprolactam, 30.6 g (1.00 mol) of 98% purity paraformaldehyde and 1.38 g of $K_2CO_3$ (0.01 mol) were brought to reaction (0.5 hours, 75° C.). The mixture was then cooled to room temperature without adding seed crystals. 145 g of reaction mixture (84.8% purity material)=123 g of methylolcaprolactam=0.86 mol=86% of the theoretical yield were obtained as an oil.

EXAMPLE 5

(comparison example)

The procedure was as in Example 2, but 2.5 mol % of acetic acid were added as the catalyst. The yield was 0.5% of the theoretical yield.

EXAMPLE 6

The batch size was as in Example 2, but 0.4 mol % of KOH were added in place of $K_2CO_3$. The yield was 87% of the theoretical yield.

EXAMPLE 7

113 g (1.00 mol) of 6-caprolactam, 30.6 g (1.00 mol) of 98% purity paraformaldehyde and 1.6 g (1.6 mol %) of triethylamine were stirred at 85° C. for 15 hours. The yield was 80% of the theoretical yield.

The following table repeats the results:

| Ex. | Catalyst | (Amount mol %) | Yield | Remark |
| --- | --- | --- | --- | --- |
| 1 | $K_2CO_3$ | (0.5) | 99.9% | |
| 2 | $K_2CO_3$ | (2.5) | 97% | |
| 3 | $K_2CO_3$ | (0.5) | 86% | Catalyst employed as a 33% strength aqueous solution |
| 4 | $K_2CO_3$ | (1.0) | 86% | Without addition of seed crystals |
| 5 | $CH_3COOH$ | (2.5) | 0.5% | |
| 6 | KOH | (0.4) | 87% | |
| 7 | $Et_3N$ | (1.6) | 80% | |

EXAMPLE 8

113 g of caprolactam, 30.61 g of paraformaldehyde, 0.69 g of $K_2CO_3$ and 7.6 g of $H_2O$ (5% by weight relative to the total batch) were brought to reaction as in Example 1. According to analysis by NMR spectroscopy, an 82% conversion to N-methylol-caprolactam was achieved.

EXAMPLE 9

113 g of caprolactam, 30.61 g of paraformaldehyde, 0.69 of $K_2CO_3$ and 7.6 g of toluene (5% by weight relative to the total batch) were brought to reaction as in Example 1. According to analysis by NMR spectroscopy, a 91% conversion to N-methylol-caprolactam was achieved. After 24 hours, it was possible to obtain 70% of the yield mentioned as crystals.

EXAMPLE 10

113 g of caprolactam, 30.61 g of paraformaldehyde, 0.69 g of $K_2CO_3$ and 16 g of heptane (10% by weight relative to the total batch) were brought to reaction as in Example 1. According to analysis by NMR spectroscopy, a 92% conversion to N-methylol-caprolactam was achieved. After 2 hours, it was possible to obtain the total yield as crystals.

What is claimed is:

1. A process for the preparation of N-methylol-caprolactam (N-hydroxymethyl-caprolactam) through reaction of caprolactam with anhydrous formaldehyde in the presence of an alkaline catalyst at elevated temperature, characterized in that the reaction is carried out substantially solvent-free at a temperature of 70° to 100° C.

2. A process according to claim 1, characterized in that the reaction is carried out at a temperature of 70° to 90° C.

3. A process according to claim 2, characterized in that the reaction is carried out at a temperature of 70° to 80°.

4. A process according to claim 1, characterized in that carrying out the process substantially solvent-free includes using up to 10% of weight of an OH group-containing solvent or using up to 20% by weight of an aprotic solvent or using a mixture of such solvents, in each case relative to the total reaction batch, or omitting solvents or diluents.

5. A process according to claim 4, characterized in that up to 20% of weight of an aprotic solvent are employed or the use of a solvent or diluent is omitted.

6. A process according to claim 5, characterized in that the use of a solvent or diluent is omitted.

7. A process according to claim 1, characterized in that the alkaline catalyst is a hydroxide of an alkali or an alkaline-earth metal, an alkali salt of a weak inorganic acid or a tertiary aliphatic amine in an amount of from 0.1 to 2.5 mole %, relative to caprolactam.

8. A process according to claim 7, characterized in that the catalyst is an alkali metal salt of a weak inorganic acid.

9. A process according to claim 8, characterized in that the catalyst is an alkali metal carbonate.

10. A process according to claim 9, characterized in that the catalyst is potassium carbonate.

11. A process according to claim 7, characterized in that the catalyst is employed in an amount from 0.25 to 1.5 mole %, relative to caprolactam.

12. A process according to claim 11, characterized in that the catalyst is employed in an amount of from 0.5 to 1 mole %, relative to caprolactam.

13. A process according to claim 7, characterized in that the catalyst is present in heterogeneous form.

14. A process according to claim 1, characterized in that seed crystals of pure N-methylol-caprolactam are added to the reaction batch after cooling to a temperature below the melting point of pure N-methylol-caprolactam.

15. A process according to claim 14, characterized in that the seed crystals are added in an amount of less than 10% by weight, relative to the total reaction batch.

16. A process according to claim 15, characterized in that the seed crystals are added in an amount from 0.0001 to 10% by weight, relative to the total reaction batch.

17. A process according to claim 16, characterized in that the seed crystals are added in an amount from 0.001 to 5% by weight, relative to the total reaction batch.

18. A process according to claim 15, characterized in that the seed crystals are added at a maximum temperature of 65° C.

19. A process according to claim 18, characterized in that the seed crystals are added at a temperature of 10° to 65° C.

20. A process according to claim 19, characterized in that the seed crystals are added at a temperature of 20° to 60° C.

* * * * *